United States Patent [19]

Winkelman et al.

[11] Patent Number: 4,542,742

[45] Date of Patent: Sep. 24, 1985

[54] HEMOSTATIC ELLIPSE GUIDE FOR CUTTING SKIN

[76] Inventors: Jeffry Winkelman; Janee D. Steinberg, both of 8709 Banyan Ct., Tamarac, Fla. 33321

[21] Appl. No.: 557,865

[22] Filed: Dec. 5, 1983

[51] Int. Cl.⁴ ............................................. A61B 17/00
[52] U.S. Cl. ................................. 128/325; 128/303 R
[58] Field of Search .................... 128/325, 303 R, 305, 128/335

[56] References Cited

U.S. PATENT DOCUMENTS

| 1,561,116 | 11/1925 | Silliman | 128/325 |
| 2,932,296 | 4/1960 | Sanders | 128/305 |
| 3,502,070 | 3/1970 | Bliss | 128/303 R |
| 4,114,624 | 9/1978 | Haverstock | 128/303 R X |
| 4,192,312 | 3/1980 | Wilson | 128/305 X |

FOREIGN PATENT DOCUMENTS 1094820  5/1955  France .............................. 128/305

OTHER PUBLICATIONS

Mueller Catalog, "The Surgical Armamentarium" (1980), p. 103.

Primary Examiner—Michael H. Thaler
Attorney, Agent, or Firm—Jacob H. Steinberg

[57] ABSTRACT

A surgical instrument which when properly used will facilitate incisional and excisional skin surgery, to be used in conjunction with conventional surgical cutting instruments.

7 Claims, 3 Drawing Figures

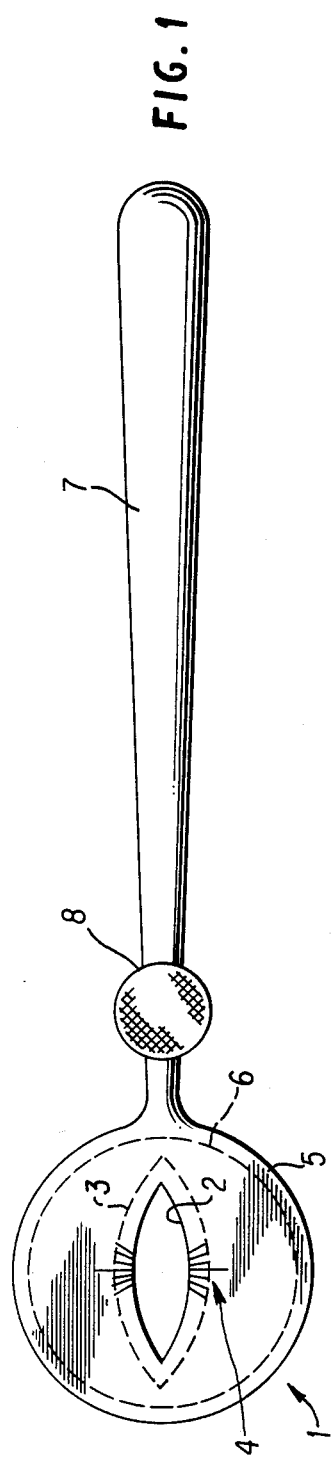
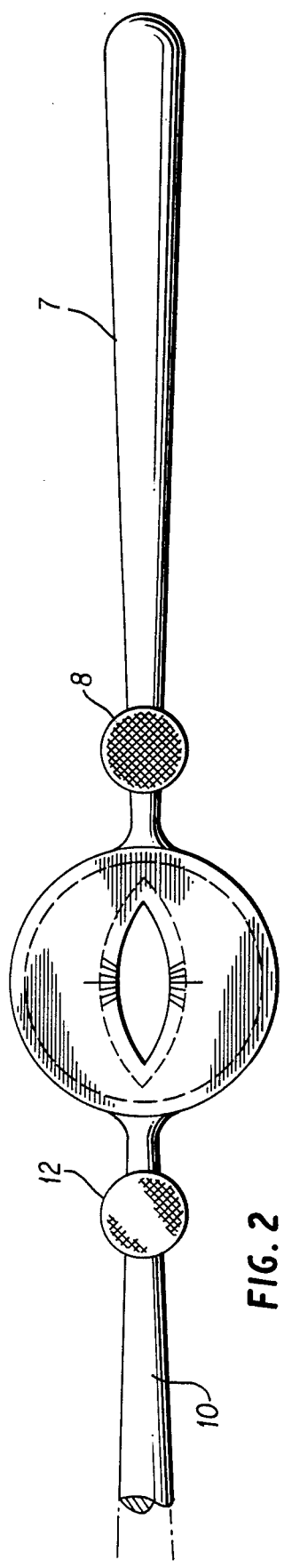
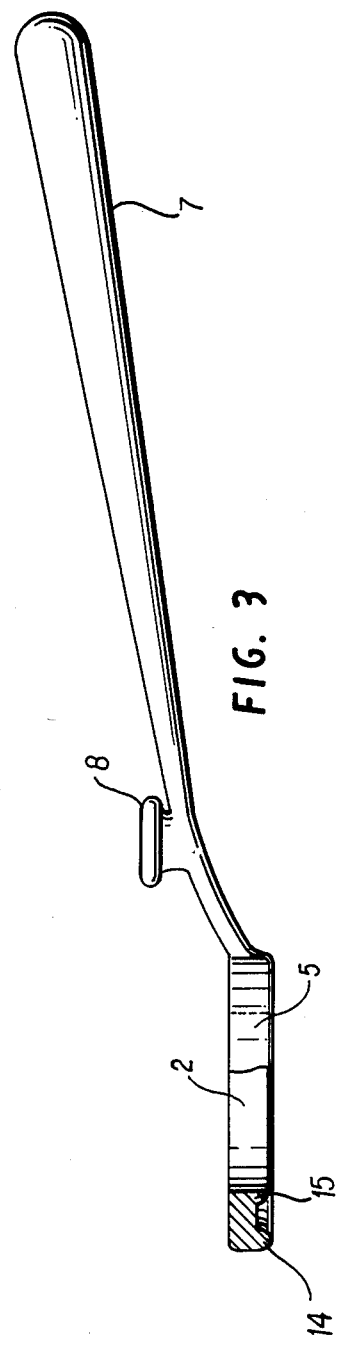

HEMOSTATIC ELLIPSE GUIDE FOR CUTTING SKIN

This invention relates to a surgical instrument that can be used as a guide for incisional and excisional cutting with surgical cutting instruments. The principle needs when cutting into a skin area wherein a diseased area is to be excised is to avoid excessive bleeding, to obtain a straight hairline scar which is aesthestically acceptable, and to permit each and every surgeon or even a qualified non-surgeon to obtain equally satisfactory results. There is a further need to maintain the skin area taut when cutting into it. Therefore, it is an object of this invention to provide a surgical instrument guide that will when used with a surgical cutting instrument answer all of these needs.

A prior art device showing a marking tool for cutting a kin area is described in the U.S. Pat. No. 3,502,072 to Bliss. It is a marker which indents the skin area causing it to turn red at the site of the indent. When the marker is removed, the surgeon must follow this red indent when cutting. This device has three major drawbacks. First, the surgeon must cut freehand with no guide to rest his cutting blade on. Second, the device provides no hemostasis, so that when the skin site is cut, the mark is obscured by blood. Third, the nature of skin is such that the instant the device is removed, the resultant marks begin to resolve, so that it is essential for the surgeon to work quickly.

It is therefore a prime object to provide a surgical skin cutting guide that would overcome all the drawbacks or disadvantages of the Bliss Marker.

A further object of this invention is to provide maximum hemostasis at the surgical site while providing a rigid metallic surface against which the side of a surgical blade can be rested as the tip and cutting edge pierce and lacerate the skin so as to create a precisely shaped wound that can be accurately reproduced and, in addition, provides for tissue tautness to the downward pressure of the surgical cutting knife.

It is a further object to provide a cutting guide having a perfectly designed symmetrical ellipse wherein its length is four times its width so that the edges of the wound can be perfectly opposed with minimum tension on the newly closed incision and be aestetically acceptable.

While some of the salient features, characteristics and advantages of the instant invention have been pointed out, others will become apparent from the following disclosure when taken in conjunction with the accompanying drawing wherein:

FIG. 1 is a top plan view of the cutting guide of this invention;

FIG. 2 is a modification of the view of FIG. 1 showing 2 handles; and

FIG. 3 is a front elevational view of FIG. 1 showing more detail of cutting guide.

In FIG. 1, there is shown a handle 7 having a knurled circular surface thumb rest 8 to allow an operator to apply considerable downward force. A circular plate 1 is provided so that when pressed against the skin the debossed circular area 5, 6 and the debossed elliptical area 2, 3 will create hemostasis at the cutting site and will keep the skin taut. At the site of the ellipse, centrally located on its surface are a series of scribe lines to enable the surgeon to properly align the area to be excised.

In FIG. 2, there is shown a second handle 10 having knurled thumb rest 12 so that an assistant can apply pressure with two hands to create more hemostatic pressure for the excision.

In FIG. 3, the debossed area of the circle 14 and the debossed area of the ellipse 15 are more clearly shown along with the angle to the horizontal to which the handle is located. This angle could be about 35° from the horizontal to assure for maximum downward pressure. With regard to the ellipse, although for small wounds a ratio of length to width is preferred to be 4 to 1, there are larger wounds which require a 3 to 1 ratio. From many trial and error instances, it has been determined that 15 to 20 lbs. per square inch is needed to provide for proper hemostasis. For a small incision a surgeon can apply this pressure with one hand, but for a larger incision an assistant is needed to assure proper pressure. For the two handled guide the small axis of the ellipse has a length of 15 mm. or greater and a long axis of 60 mm. or greater. It is also pointed out that to prevent sliding of the cutting guide on the skin surface, the top area of the debossed ellipse is very slightly knurled.

When a surgeon is to make an excision of a skin area, he holds the handle by locking his fingers of one hand on the handle, applying pressure with his thumb. When applying 15 to 20 lbs. of pressure, hemostasis occurs at the site of the surgical area, at the circular area of the plate and the elliptical area of the plate. At the same time, the site of the skin area to be cut is kept taut, especially since the slightly knurled debossed areas will stay fixed on the skin area to which it is applied. The scribe lines enable the surgeon to properly align the ellipse over the area to be excised. Since 15 to 20 lbs. per square inch is needed in some instnaces, it will be necessary to use an assistant. When the surgeon pierces the skin, the area to be cut is taut and has very little blood because of the dual hemostasis elements. The blade rests against the metal ellipse serving as a guide for the knife which then cuts a perfect elliptical pattern. Since the size of an excised area can vary from small to large, a series of different sizes of the HEG (hemostatic ellipse guide) is provided in sizes by 5 mm. increments in the short axis of the ellipse going up to 30 mm. The size of the cutting guide to be used is dependent upon the size of the lesion to be excised. It should be noted that a zone of normal skin (from 1 mm. to 10 mm.) will always be removed with the pathologic entity. The long axis of the ellipse can range from 20 mm. to 120 mm. The depth of the debossed areas is 1.5 mm. This cutting guide is made of metal which could be coated with an insulative plastic resin so that it can be used in conjunction with electrosurgical cutting and coagulating instruments. It is easily sterilizable between uses, and economical because of its long life.

To sum up the advantages provided by the use of this surgical cutting guide include:

1. Hemostasis in the area to be cut.
2. Tautness of the skin for incision of the blade and cutting.
3. An elliptical guiding edge along which a surgical blade can rest while cutting.
4. A reproducible elliptical cutting blade guide for use of any surgeon or skilled assistant.

While the instant invention has been hereinabove described in connection with skin surgery for the removal of discrete pathologic entities, it will be apparent to those skilled in the art that this cutting guide may be utilized for other purposes. For example, the guide may be used to excise exactly equal amounts of redundant tissue from any part of the body so as to improve the appearance via plastic surgery.

It will also be apparent to any skilled surgeon that numerous modifications can be made in the invention without departing from its scope and spirit. Accordingly, no limitations are intended except in so far as specifically set forth in the following claims.

What is claimed is:

1. A surgical hemostatic cutting guide for a surgical knife comprising a circular plate having an upper and lower side and provided with an elliptical debossed pattern centrally located on said plate and a circular debossed pattern located circumferentially of said plate and having an inclined handle which is provided with a circular knurled thumb rest, both of said debossed patterns being located on the lower side of said plate and an elliptical opening located centrally in said plate inside of said elliptical debossed pattern, said elliptical opening forming an elliptical guiding edge along which a surgical blade can rest while cutting.

2. The cutting guide of claim 1 wherein the elliptical patterned surface is provided with scribe lines.

3. The cutting guide of claim 1 wherein a second handle and thumb rest is provided on the opposite side for use with an assistant.

4. The cutting guide of claim 1 wherein the ratio of the short axis to the long axis of the ellipse is 1:4.

5. The cutting guide of claim 1 wherein the ratio of the short axis to the long axis of the ellipse is 1:3.

6. The cutting guide of claim 1 wherein different sizes of the elliptical cutting pattern are provided, ranging in size from 5 mm on the short axis to 30 mm in 5 mm increments while the long axis ranges from 20 mm to 120 mm.

7. The cutting guide of claim 1 wherein the surface of the debossed areas are slightly knurled.

* * * * *